US009445800B2

(12) United States Patent
Nguyen

(10) Patent No.: US 9,445,800 B2
(45) Date of Patent: Sep. 20, 2016

(54) MINIMALLY INVASIVE LAPAROSCOPIC RETRACTOR

(75) Inventor: Hien Tan Nguyen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 63 days.

(21) Appl. No.: 13/978,200

(22) PCT Filed: Jan. 4, 2012

(86) PCT No.: PCT/US2012/020138
§ 371 (c)(1),
(2), (4) Date: Oct. 14, 2013

(87) PCT Pub. No.: WO2012/094364
PCT Pub. Date: Jul. 12, 2012

(65) Prior Publication Data
US 2014/0031630 A1    Jan. 30, 2014

Related U.S. Application Data

(60) Provisional application No. 61/429,648, filed on Jan. 4, 2011, provisional application No. 61/450,682, filed on Mar. 9, 2011.

(51) Int. Cl.
*A61B 17/02* (2006.01)
*A61B 1/32* (2006.01)
*A61B 17/00* (2006.01)

(52) U.S. Cl.
CPC ............ *A61B 17/0218* (2013.01); *A61B 1/32* (2013.01); *A61B 17/02* (2013.01); *A61B 17/0281* (2013.01); *A61B 2017/00557* (2013.01); *A61B 2017/0212* (2013.01)

(58) Field of Classification Search
CPC .......... A61B 1/32; A61B 2017/00557; A61B 17/02; A61B 2017/0212; A61B 17/0218; A61B 17/0281
See application file for complete search history.

(56) References Cited

U.S. PATENT DOCUMENTS 5,163,949 A   11/1992  Bonutti et al.
5,195,507 A    3/1993  Bilweis
(Continued)

FOREIGN PATENT DOCUMENTS

CN   101873832   10/2010
CN   201701244    1/2011
(Continued)

OTHER PUBLICATIONS

Machine Translation of FR 2726993 obtained from EPO website <http://translationportal.epo.org/emtp/translate/?ACTION= description-retrieval&COUNTRY=FR&ENGINE=google&FORMAT=docdb&KIND=A1&LOCALE=en_EP&NUMBER= 2726993&OPS=ops.epo.org/3.1&SRCLANG=fr&TRGLANG= en> on Mar. 25, 2015.*

(Continued)

*Primary Examiner* — Larry E Waggle, Jr.

(57) ABSTRACT

An inflatable retractor for use in laparoscopic surgery of a patient's body includes an inflatable element disposed at a distal end of a retractor shaft. The retractor shaft includes a port for receiving insufflating fluid. The inflatable element is designed so that different parts of the inflatable element may be filled to different pressure levels. The inflatable element may include separately inflatable chambers. In this way, the rigidity and shape of the inflatable element is controlled by the surgeon, allowing for flexibility and ease of use.

32 Claims, 11 Drawing Sheets

(56) References Cited

U.S. PATENT DOCUMENTS

| | | | |
|---|---|---|---|
| 5,308,327 A | | 5/1994 | Heaven et al. |
| 5,318,586 A | | 6/1994 | Ereren |
| 5,359,995 A | | 11/1994 | Sewell, Jr. |
| 5,379,759 A | * | 1/1995 | Sewell, Jr. .......... A61B 17/0218 600/207 |
| 5,400,773 A | | 3/1995 | Zhu et al. |
| 5,520,609 A | | 5/1996 | Moll et al. |
| 5,588,951 A | | 12/1996 | Zhu et al. |
| 5,613,937 A | | 3/1997 | Garrison et al. |
| 5,649,902 A | * | 7/1997 | Yoon ................................ 604/1 |
| 5,772,680 A | | 6/1998 | Kieturakis et al. |
| 5,836,871 A | | 11/1998 | Wallace et al. |
| 5,865,728 A | * | 2/1999 | Moll et al. .................... 600/204 |
| 5,992,680 A | | 11/1999 | Smith |
| 6,032,671 A | | 3/2000 | Mollenauer et al. |
| 6,036,641 A | | 3/2000 | Taylor et al. |
| 6,146,401 A | | 11/2000 | Yoon et al. |
| 7,758,500 B2 | | 7/2010 | Boyd et al. |
| 2003/0225432 A1 | * | 12/2003 | Baptiste et al. ............. 606/191 |
| 2004/0097792 A1 | | 5/2004 | Moll et al. |
| 2004/0127931 A1 | | 7/2004 | Kincaid et al. |
| 2005/0203344 A1 | * | 9/2005 | Orban et al. .................. 600/204 |
| 2005/0245960 A1 | * | 11/2005 | Grundeman ................... 606/192 |
| 2008/0300618 A1 | | 12/2008 | Gertner |
| 2009/0137984 A1 | | 5/2009 | Minnelli |
| 2009/0287046 A1 | | 11/2009 | Yamatani |
| 2010/0016674 A1 | * | 1/2010 | Mills .............................. 600/207 |
| 2010/0069947 A1 | | 3/2010 | Sholev et al. |
| 2010/0168523 A1 | | 7/2010 | Ducharme |
| 2011/0040152 A1 | | 2/2011 | Kim et al. |
| 2011/0054408 A1 | | 3/2011 | Wei et al. |
| 2011/0190781 A1 | * | 8/2011 | Collier ............. A61B 17/00234 606/114 |
| 2015/0057501 A1 | | 2/2015 | Livne et al. |
| 2015/0245828 A1 | | 9/2015 | Harari et al. |

FOREIGN PATENT DOCUMENTS

| | | | | |
|---|---|---|---|---|
| CN | 102028511 | | 4/2011 | |
| FR | 2726993 A1 | * | 5/1996 | ............. A61B 17/02 |
| FR | 2737401 | | 2/1997 | |
| JP | 06-507810 A | | 9/1994 | |
| JP | 10-511589 A | | 11/1998 | |
| JP | 2003-164459 A | | 6/2003 | |
| WO | WO-92/21291 A2 | | 12/1992 | |
| WO | WO 92/21293 | | 12/1992 | |
| WO | WO-92/21293 A1 | | 12/1992 | |
| WO | WO 94/16630 | | 8/1994 | |
| WO | WO-96/20749 A1 | | 7/1996 | |
| WO | WO 97/32514 | | 9/1997 | |
| WO | WO-99/20321 A2 | | 4/1999 | |
| WO | WO 02/28331 | | 4/2002 | |
| WO | WO-2005/102185 A1 | | 11/2005 | |
| WO | WO 2009/144729 | | 12/2009 | |
| WO | WO 2010/042844 | | 4/2010 | |
| WO | WO 2010/078315 | | 7/2010 | |
| WO | WO-2010/078315 A1 | | 7/2010 | |
| WO | WO 2013/144959 | | 10/2013 | |

OTHER PUBLICATIONS

Extended European Search Report issued Jun. 25, 2015 in European Patent Application No. 12732225.3.
International Preliminary Report on Patentability Dated Oct. 9, 2014 From the International Bureau of WIPO Re. Application No. PCT/IL2013/050280.
International Preliminary Report on Patentability Dated Oct. 9, 2014 From the International Bureau of WIPO Re. Application No. PCT/US2012/020138.
International Search Report and the Written Opinion Dated Sep. 6, 2013 From the International Searching Authority Re. Application No. PCT/IL2013/050280.
Invitation to Pay Additional Fees Dated Jul. 16, 2013 From the International Searching Authority Re. Application No. PCT/IL2013/050280.
Notification of Reasons for Refusal Dated Nov. 17, 2015 From the Japanese Patent Office Re. Application No. 2013-547730 and Its Translation Into English.
Notification of Office Action and Search Report Dated Jul. 27, 2015 From the State Intellectual Property Office of the People's Republic of China Re. Application No. 201380027547.4 and Description of Office Action in English.
Notification of Office Action Dated Jan. 7, 2015 From The State Intellectual Property Office of the People's Republic of China Re. Application No. 201280004574.5 and Its Summary in English.
Notification of Office Action Dated Sep. 30, 2015 From The State Intellectual Property Office of the People's Republic of China Re. Application No. 201280004574.5 and Its Summary in English.
Official Action Dated Feb. 25, 2016 From the US Patent and Trademark Office Re. U.S. Appl. No. 14/387,241.
Reasons for Rejection Dated Apr. 5, 2016 From the State Intellectual Property Office of the People's Republic of China Re. Application No. 201380027547.4 and Its Translation Into English.
Supplementary European Search Report and the European Search Opinion Dated Nov. 12, 2015 From the European Patent Office Re. Application No. 13767950.2.

* cited by examiner

MINIMALLY INVASIVE LAPAROSCOPIC RETRACTOR

CROSS-REFERENCE TO RELATED APPLICATIONS

This application is a 35 U.S.C. §371 U.S. national entry of International Application PCT/US12/20138 having an international filing date of Jan. 04, 2012, which claims the benefit of U.S. Provisional Application No. 61/429,648 filed Jan. 04, 2011 and U.S. Provisional Application No. 61/450,682 filed Mar. 09, 2011, the content of each of the aforementioned applications is herein incorporated by reference in their entirety.

FIELD OF THE INVENTION

The present invention pertains to a retractor for use in laparoscopic surgery. More particularly, the present invention pertains to a minimally invasive inflatable retractor for use in laparoscopic surgery.

BACKGROUND OF THE INVENTION

Laparoscopic surgery, also known as minimally invasive surgery, is becoming an increasingly popular method of surgery. The number of surgeons graduating each year with advance minimally invasive training continues to increase, which means that the number of minimally invasive abdominal cases will also increase. One of the most challenging aspects of laparoscopic surgery is to be able to clearly visualize the organ of concern without having to constantly clear away intestines or other nearby organs from falling into the operative field.

For example, the removal of an inflamed appendix requires the surgeon to be able to isolate this organ from its nearby surrounding tissues, such as the colon, sigmoid, ileum, jejunum, ovaries, etc. If this operation were performed openly, through a large incision, then the surgeon has the option of using sterile towels to push the other intestines and organs away from the inflamed appendix, thereby creating a clear visual field for the safe removal of the organ.

Laparoscopically, the surgeon does not have the option of using a sterile towel. The frustration is amplified by the fact that the visualized operative field through a laparoscope is very narrow and close-up, and the avalanche of intestines into the operative field is often visualized suddenly at a critical part of the dissection process. Therefore, the surgeon must constantly "clear the field" by constantly pushing the adjacent organs away as they fall back and cover up the appendix, or try to utilize the tilt function of the operating room table to hopefully allow the adjacent organs to fall away from the operative field. This is an inconsistent method of isolating the operative field, which leads to an inefficient and sometimes dangerous operation.

Various tools have been developed for retracting organs from the field of vision during surgery. However, some of these tools themselves have been known to impart damage to the organs themselves.

Accordingly, there is a need in the art for a retractor for laparoscopic surgery that removes organs from the field of vision safely and effectively.

SUMMARY

According to a first aspect of the present invention, an inflatable retractor comprises an inflatable element including an inner surface and an outer surface and a retractor shaft including a port for receiving insufflation pressure, wherein the inflatable element is attached to a distal end of the retractor shaft. The inflatable element is configured so as to form a compartment for retaining the organ when the inflatable element is insufflated with fluid.

According to a second aspect of the present invention, an inflatable retractor comprises an inflatable element including at least a first chamber and a second chamber and a retractor shaft including a port for receiving insufflating pressure. The inflatable element is secured to a distal end of said retractor shaft. The inflatable element is configured so as to form a compartment when the inflatable element is insufflated with fluid. By using the term fluid, we also refer to air as a particular type of fluid that is useful.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

Figure 1:
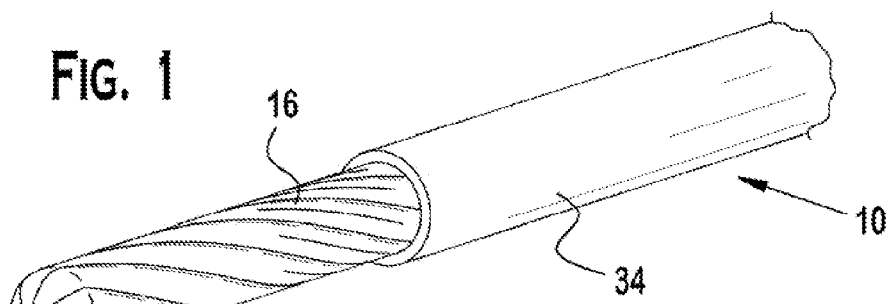
FIG. 1 illustrates a perspective view of an exemplary retractor, in part, according to the features of the present invention showing the inflatable element in a deflated position.

The present invention pertains to an inflatable retractor used in laparoscopic surgery to retract organs from the field of vision so that laparoscopic surgery of a particular organ may be performed. However, it should be understood that the inflatable retractor of the present invention is not limited to laparoscopic use, but may be applied to a wide variety of procedures, including open surgery, thoracic surgery, and endoluminal surgery.

With reference to FIGS. 1-10, an inflatable retractor 10 includes an inflatable element 12 having an inner surface 14 and an outer surface 16, and disposed at a distal end of a retractor shaft 18, as shown, for example, in FIGS. 2-4 and 6-10. The inflatable element 12 is configured such that, when deflated, the inflatable element can be wrapped around the distal end of the shaft 12, and when inflated, the inflatable element 12 opens up like an umbrella to trap organs therein. In this way, the retractor 10 can be easily deployed without causing interference when in the deflated condition, while providing a substantial device that allows retraction of major organs when in the inflated condition.

Figure 4:
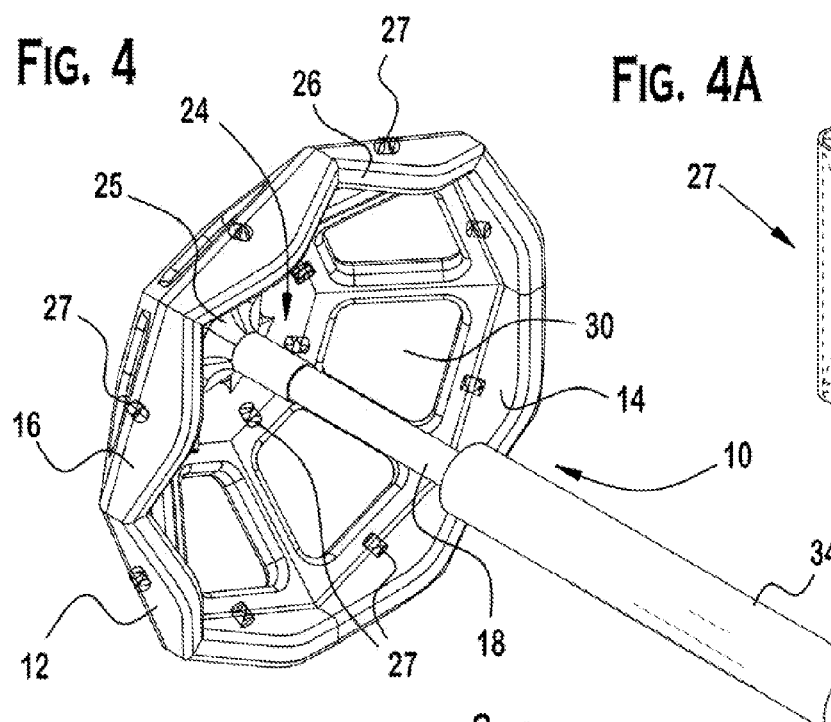
FIG. 4 illustrates a perspective view of the exemplary retractor in an inflated position according to the features of the present invention.
Figure 11:
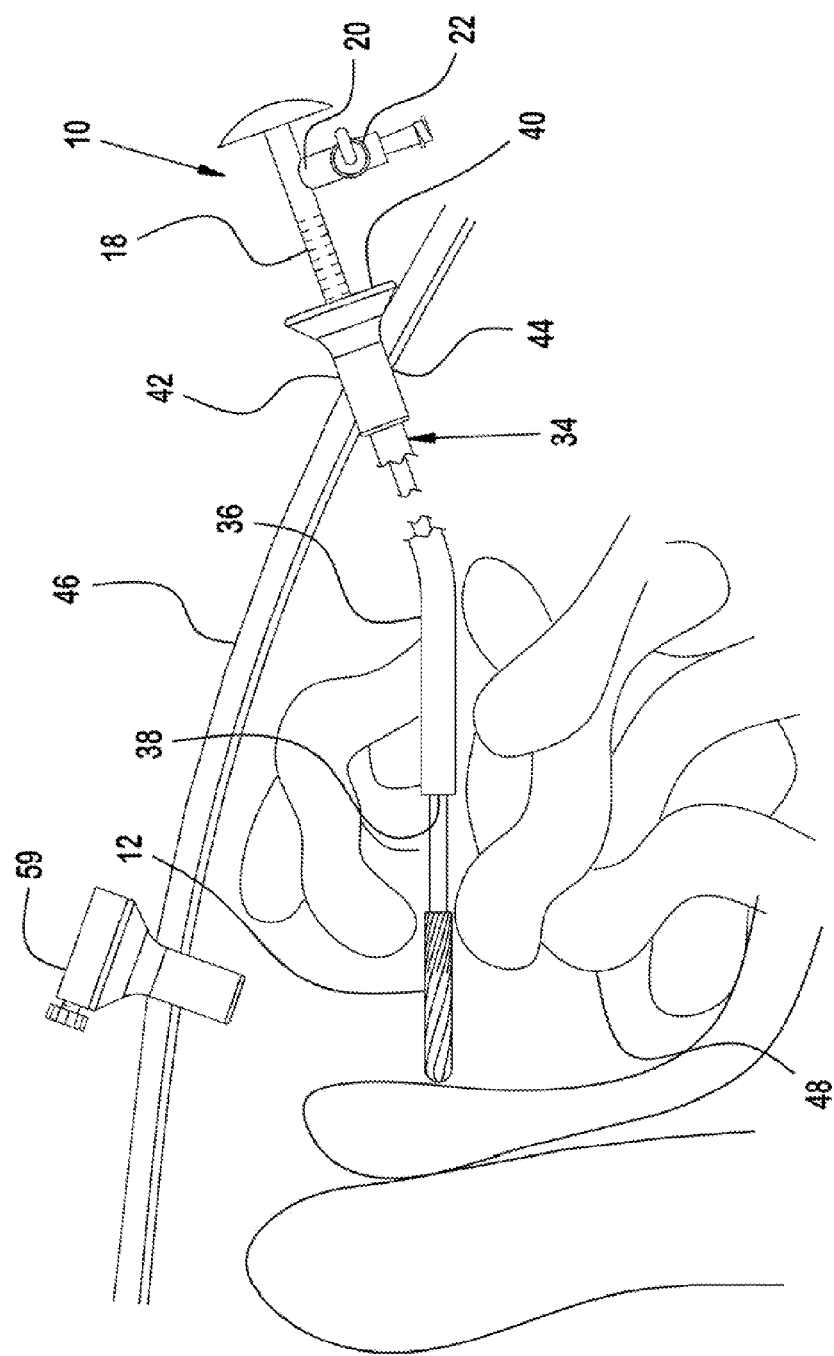
FIG. 11 illustrates a partial schematic view of a patient during laparoscopic surgery illustrating initial deployment of the inflatable retractor according to features of the present invention.
Figure 12:
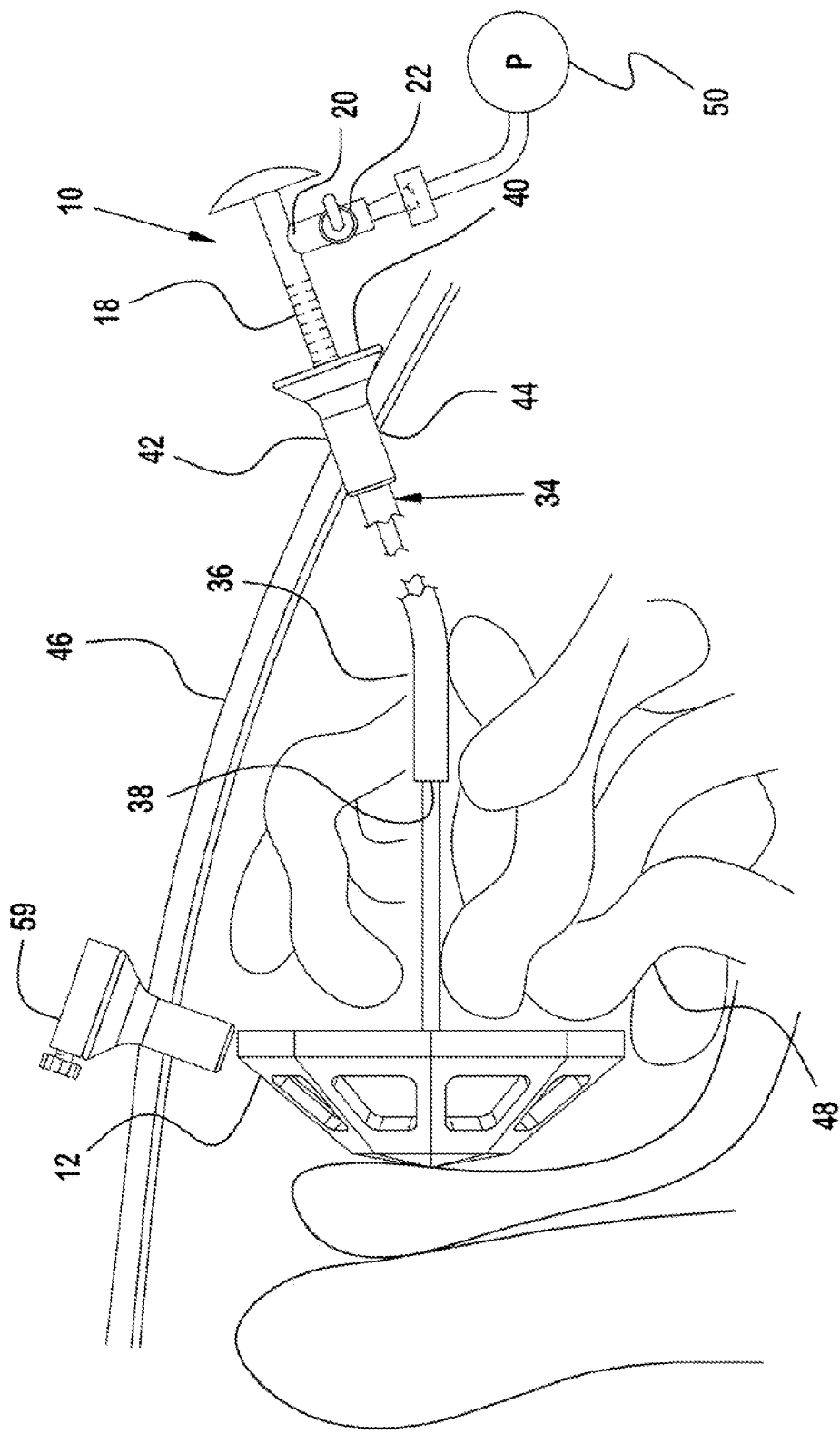
FIG. 12 illustrates a partial schematic view of a patient during laparoscopic surgery illustrating insufflation of the inflatable retractor according to features of the present invention.
Figure 13:
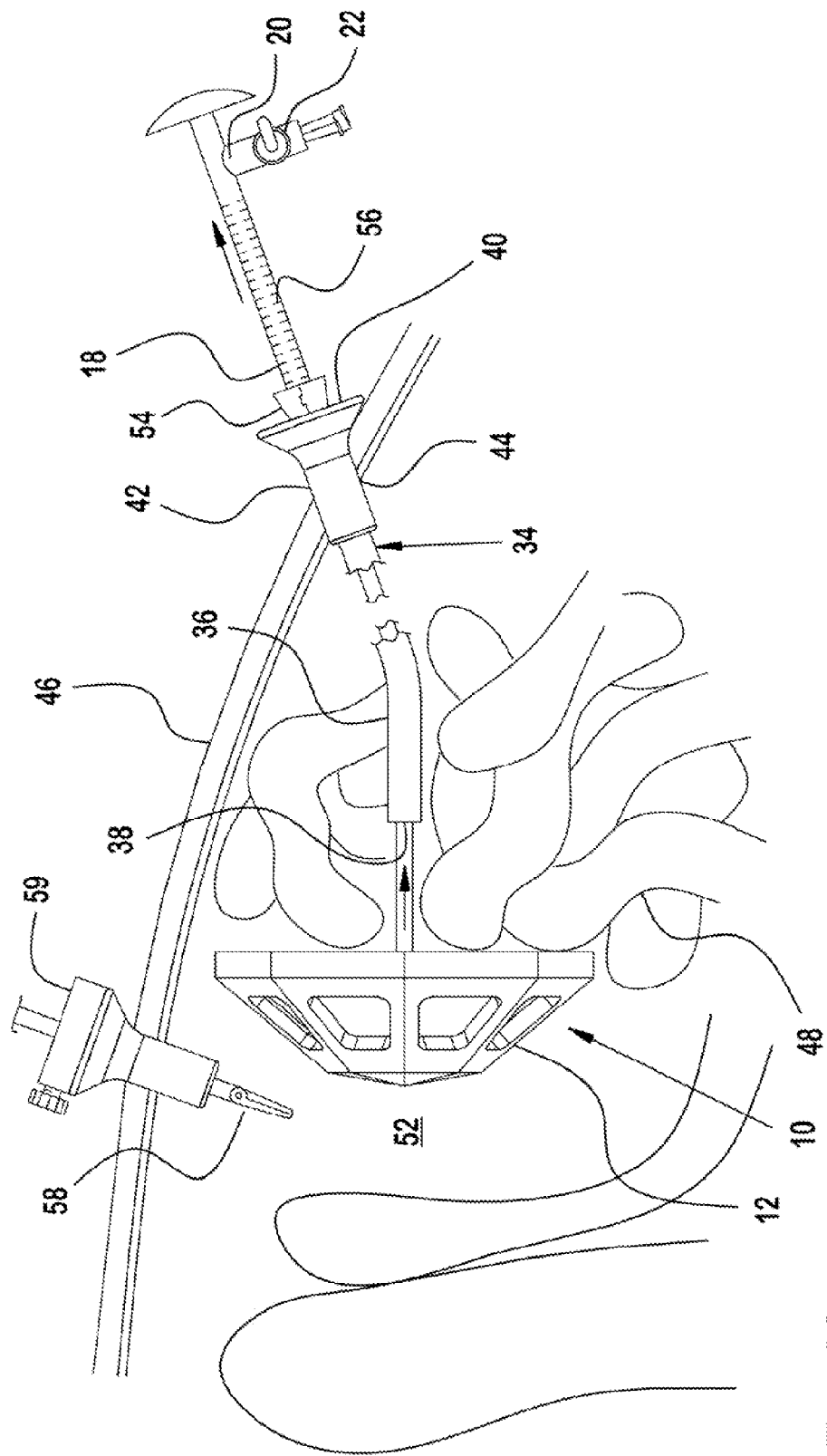
FIG. 13 illustrates a partial schematic view of a patient during laparoscopic surgery illustrating engagement of the bowels by the inflatable retractor according to features of the present invention.

To insufflate the inflatable element 12, the retractor shaft 18 is hollow and includes a port 20 which communicates with an internal channel (not shown) for receiving insufflating fluid such as air (FIG. 4), which causes the inflatable element 12 to expand and inflate. The size of the internal channel of the retractor shaft may be sufficiently large to allow another laparoscopic instrument (e.g., a grasper) to be deployed through the internal channel, thereby allowing the retractor 10 be used as an extended trocar. A 5 mm camera may also be placed through the internal channel of the retractor 10 to minimize visual impedance by the retractor 10. In addition, while the port 20 is shown in FIG. 4 as being at the proximal end of the retractor shaft 18, it should be understood that it may be at any location on the retractor shaft 18 that remains outside the patient's body during the procedure. For example, FIGS. 11-13 show the port 20 being located at the side of the retractor shaft 18. In this way, a valve 22 is associated with port 20 to allow a surgeon to control insufflating the inflatable element 12.

With reference back to FIG. 4, the inflatable element 12 is configured so as to form a compartment 24 when the inflatable element 12 is insufflated with fluid. A "compartment" is hereby defined as a 3-dimensional volumetric space, which can retain organs therein. In this way, a "compartment" is like a bowl or an upside down umbrella, so that at least a portion of the organ or tissue can be constrained inside the compartment. As such, the compartment 24 acts to trap organs behind it, so that organs may be cleared from the field of vision. As shown in FIG. 4, the compartment 24 is preferably umbrella shaped. However, the compartment 24 may be any other shape, depending upon application and design preference. For example, the compartment 24 may be flatter and v-shaped to bluntly isolate organs, such as the gallbladder, or for safe dissection of adhesed intra-abdominal planes.

Similarly, the inflatable element 12 is shown as being circular. However, other shapes are possible, including but not limited to, oval, rectangular, diamond, triangular, or square. In addition, while the inflatable element 12 is shown as being symmetrical, it should be understood that the inflatable element 12 may be asymmetrical, depending on application and design preference. In this way, the inflatable element 12 may be manufactured to any specific size or configuration to accommodate the operation, depending on application and design preference.

Preferably, the inflatable element 12 is made from a material that becomes rigid once inflated and has a sufficient tensile strength to hold large organs, such as the bowels that could weigh as much as 5 pounds. In addition, the inflatable element 12 is preferably made of an inert compound, so as to not aggravate patients with latex allergies. Examples of materials include, but are not limited to, any plastic or polymer based materials, such as polyurethane, silicone, and polyethylene.

In addition, the inflatable element 12 should be sufficiently sized and configured to hold particular organs at issue. For example, in the case of retracting bowels, the width of the inflatable element 12 may be up to 50-75% of the cross sectional view of the abdominal cavity. In addition, inflatable element 12 should be sufficiently thick so as to prevent the inflatable element 12 from turning inside out. However, other sizes and shapes are possible, depending upon application and design preference. Similarly, the retractor shaft 18 should be made from a material that is rigid and sturdy, and able to hold the inflatable element 12 and the organs retained therein. Such materials include, but are not limited to, polyethylene, silicone, polyurethane or any plastics or polymer based material.

To further prevent the inflatable element 12 from turning inside out, a support structure 25 may be positioned between the inflatable element 12 and the retractor shall 18 (FIG. 4). Preferably, the support structure 25 is configured and sized to provide maximum support, while taking up minimum space. In the preferred embodiment, the support structure 25 is inflatable and made from the same material as the inflatable element 12. However, the particular shape, configuration and material of the support structure 25 will depend upon application and design preference.

Figure 4A:
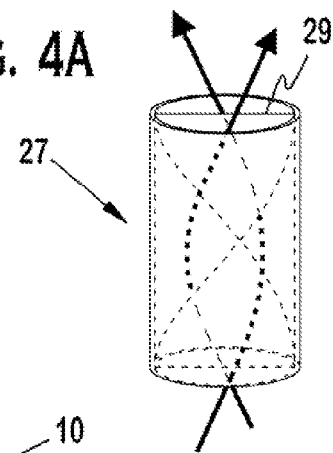
FIG. 4A illustrates a perspective view of a valve to be used in connection with the exemplary retractor according to the features of the present invention.
Figure 5:
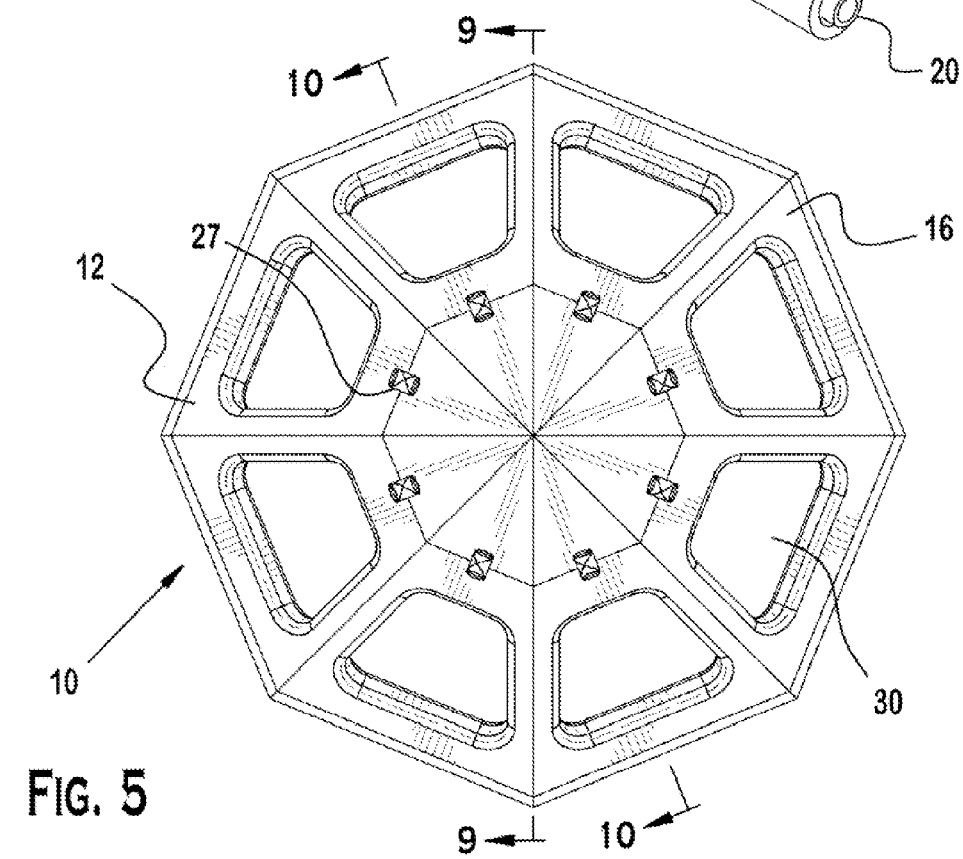
FIG. 5 illustrates a top plan view of the exemplary retractor in an inflated position according to the features of the present invention.
Figure 7:
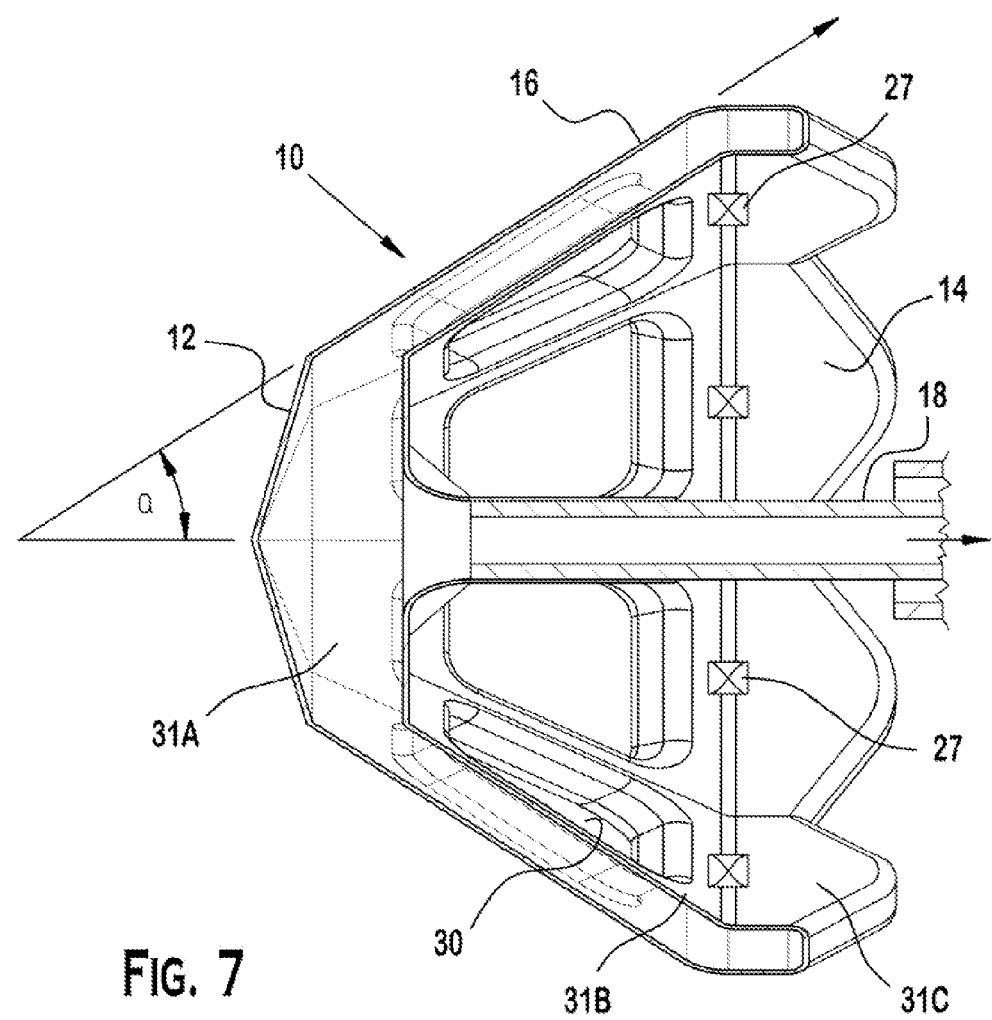
FIG. 7 illustrates a cross sectional view of the inflatable element in a partially inflated position according to features of the present invention.

With reference to FIGS. 4, 5, and 7, valves 27 are provided at various locations within the inflatable element 12 to control insufflation of various parts of the inflatable element 12. With reference to FIG. 4A, the valve 27 is configured to include a partition 29 down the middle, which may be twisted 90 to 180 degrees, which acts as a flow restrictor. The twistable partition 29 makes it a plug at low insufflation pressures, which requires more back pressure to insufflate the first compartment. After adequate insufflation, it allows air to pass and fill up the second compartment, to allow for "staged" insufflation of the retractor 10.

According to a preferred embodiment as shown in FIGS. 4, 5, and 7, the valves 27 are placed at strategic locations between the inner surface 14 and outer surface 16 of the inflatable element 12 so as to form staged insufflation of the inflatable element 12. According to the preferred embodiment shown in FIG. 4A, staged insufflation may proceed, whereby the first insufflatable chamber 31A is filled first (see FIG. 7), followed by the second insufflatable chamber 31B, and then the third insufflatable chamber 31C.

For example, the inflatable element 12 may be designed such that when the first inflatable chamber 31A reaches a predetermined insufflation pressure, the valves 27 positioned between the first inflatable chamber 31A and second inflatable chamber 31B open to allow fluid into the second inflatable chamber 31B. Similarly, when the second inflatable chamber 31B reaches a predetermined insufflation pressure, the valves 27 positioned between the second inflatable chamber 31B and the third inflatable chamber 31C open to allow fluid into the third inflatable chamber 31C.

Figure 15A:
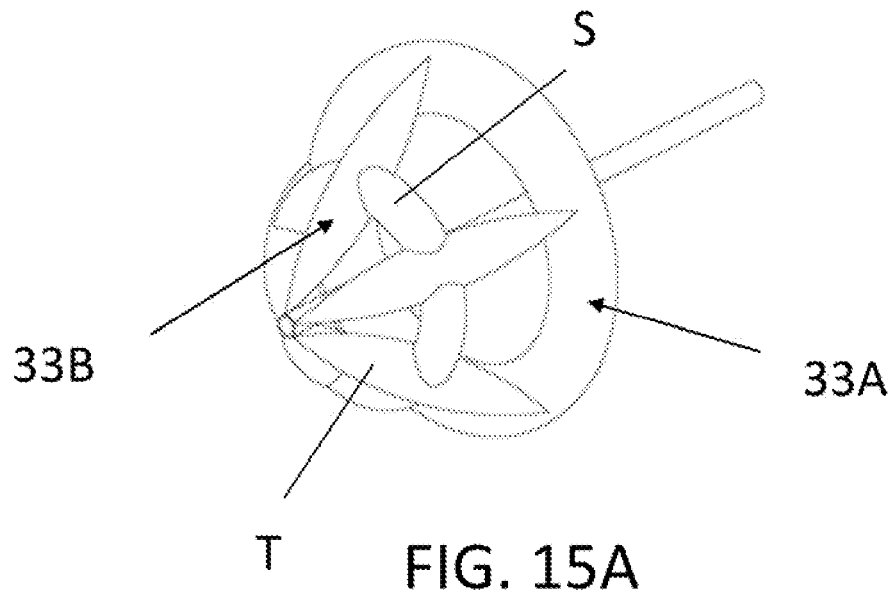
FIG. 15A illustrates a perspective view of another exemplary embodiment of the inflatable retractor according to features of the present invention.
Figure 15B:
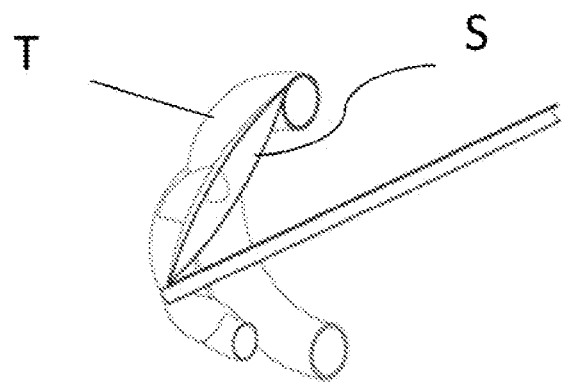
FIG. 15B illustrates a perspective view of the inflatable retractor of FIG. 15B, with the crown removed.

In another exemplary embodiment as shown in FIGS. 15A and 15B, two independent and separate chambers 33A and 33B are illustrated. In this way, one or more tubes may be used to insufflate each chamber independently, allowing for varying pressures in each chamber. For example, the outer rim or crown 33A of the inflatable element 12 may be filled with less pressure so as to minimize damage to bowels during retraction, while a rigid base with a greater pressure would provide more stability to the device. The second chamber 33B may include support elements S, connected by an extra tubular section T, which connects the tubular section T and support elements S to a single sphere.

Accordingly, the insufflation pressure of the different chambers 33A and 33B may be controlled by the user to obtain specific and/or different pressures in each chamber. In addition, each of the support elements S may be separately inflatable, allowing for an asymmetric pumping of the inflatable element, thereby achieving a single larger side observation window.

Figure 10:
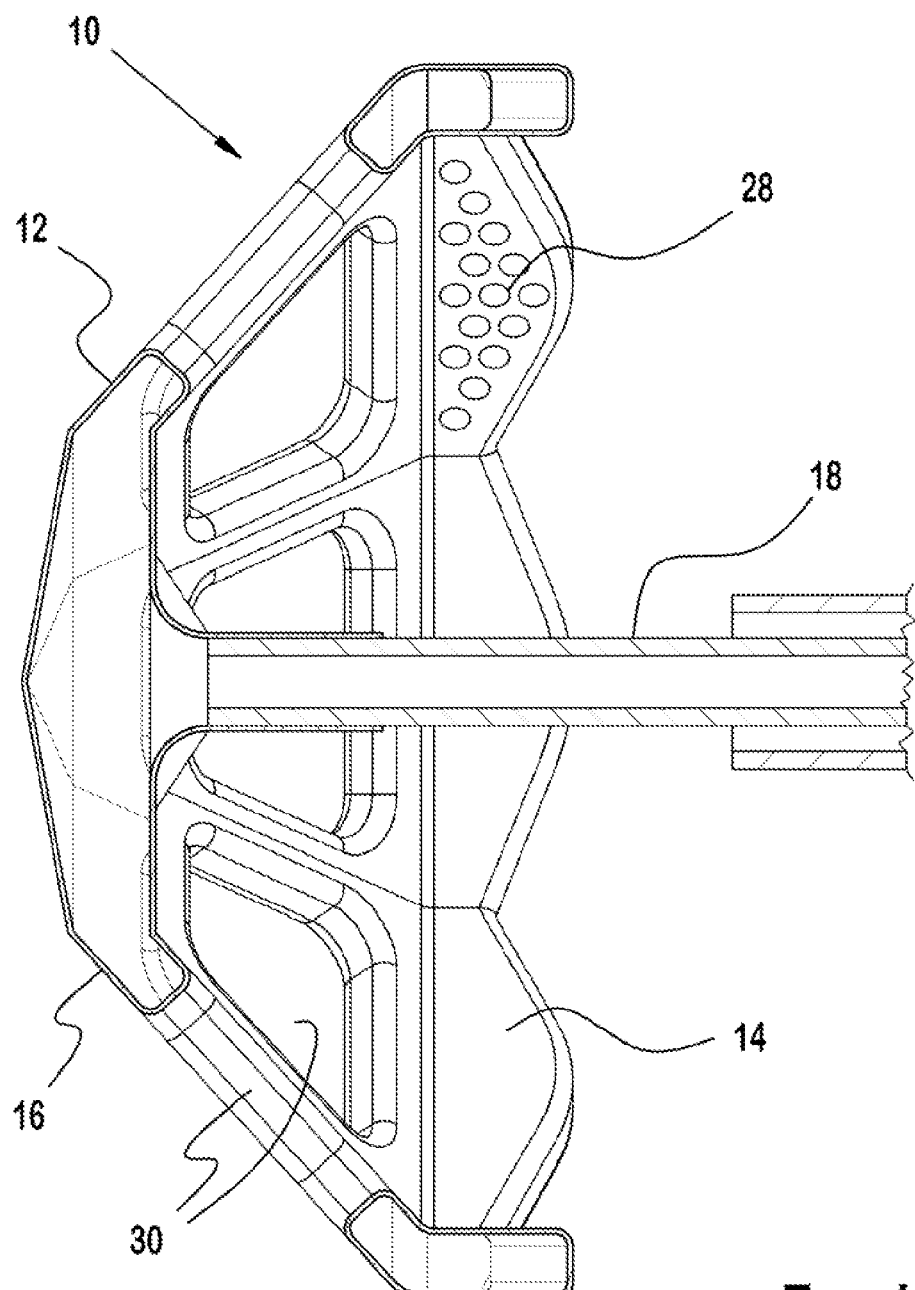
FIG. 10 illustrates a cross sectional view of the inflatable element in an inflated position and showing optional bumps according to features of the present invention.

While two chambers are shown in the exemplary embodiment, it should be understood that any number of chambers may be used depending upon application and design preference. To aid in attachment to surrounding tissue to maximize retraction potential, the inner surface 14 may include bumps 28, as shown in FIG. 10. In addition, the outer edge 26 of the inflatable element 12 (FIG. 4) may be wedged or scalloped, to further aid in adhesion of the surrounding tissue. Importantly, there should be no sharp edges or hard substances on the inflatable element 12 to potentiate bowel injury or vessel damage. However, the bumps 28 and wedged outer edge 26 are not necessary, particularly if inflatable element 12 is made from material having a sufficiently high surface roughness.

Figure 3:
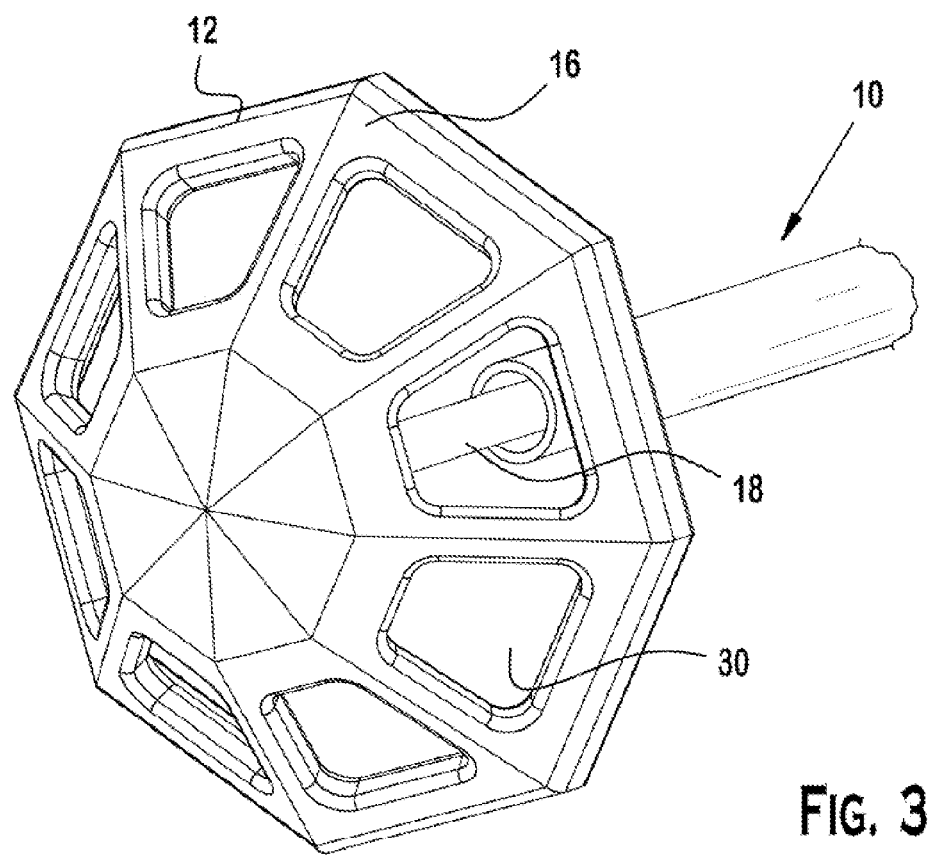
FIG. 3 illustrates a perspective view of the exemplary retractor in an inflated position according to the features of the present invention.

With reference to FIGS. 3-5, a plurality of windows 30 may be disposed through the inflatable element 12. The windows 30 should be sufficiently large so as to enable a field of vision beyond the outer surface 16 of the retractor 10. That is, the windows 30 should be sized to allow the surgeon to see behind the retractor 10. The windows 30 may be any size or shape, and in any pattern or configuration, depending on application and design preference. In addition, the windows 30 also should be sufficiently sized to allow for other instruments to be positioned there through, as will be described in more detail below.

Figure 8:
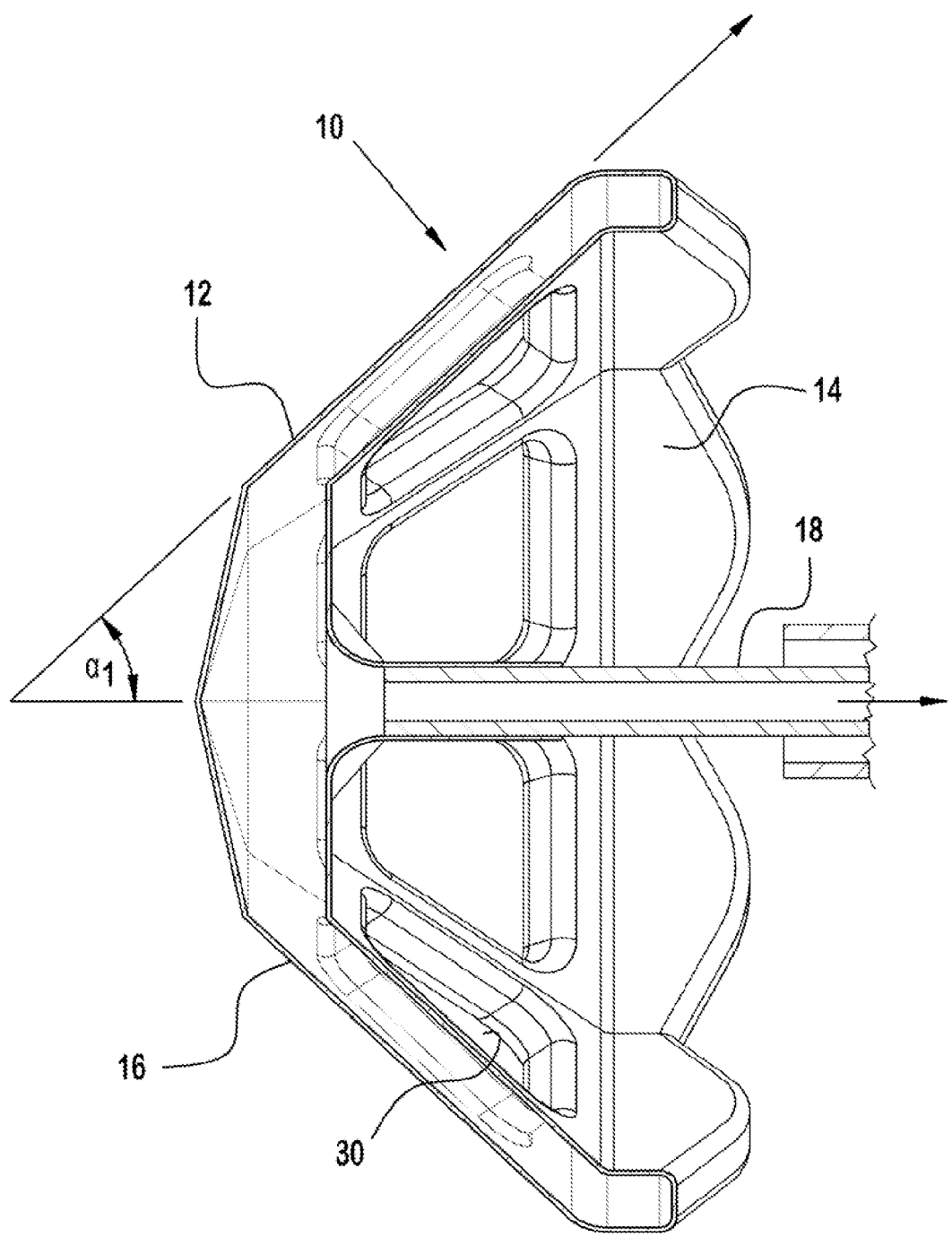
FIG. 8 illustrates a cross sectional view of the inflatable element in another partially inflated position according to features of the present invention.
Figure 9:
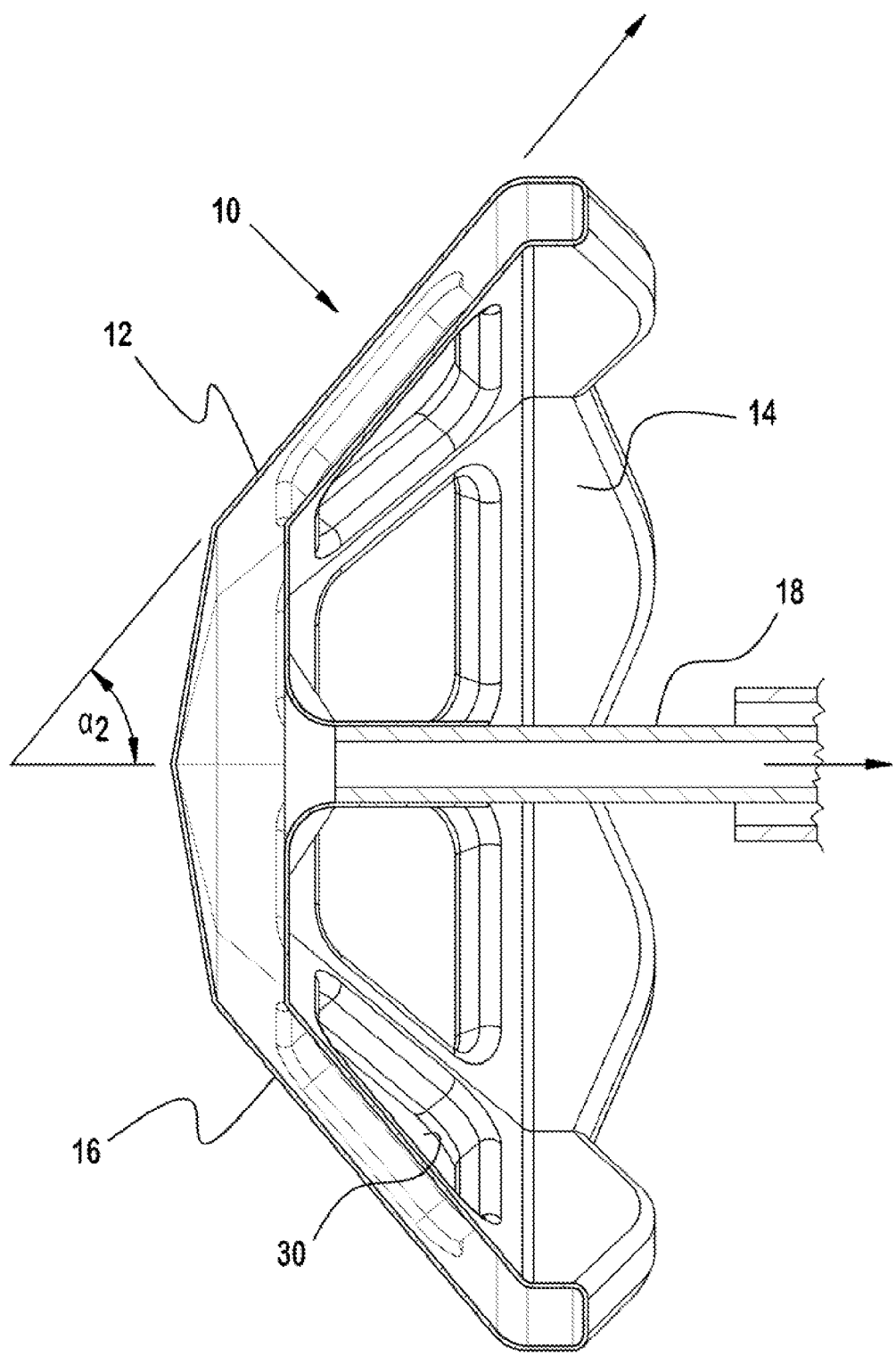
FIG. 9 illustrates a cross sectional view of the inflatable element in a fully inflated position according to features of the present invention.

With reference to FIGS. 7-9, the inflatable element 12 may be insufflated to different levels, such that a configuration of the compartment 24 changes according to the insufflating level. For example, in the particular embodiment shown in FIGS. 7-9, the amount of concavity of the inflatable element 12 is adjustable by changing the insufflation pressure of the inflatable element 12. As shown in FIG. 7, a more compact, deeper compartment is possible when the inflatable element 12 is insufflated to a lower level. In this way, the angle α formed between a longitudinal axis of the retractor shaft 18 and a predominant axis of the inflatable element 12 is relatively small. Comparatively, a flatter compartment is shown in FIG. 8, wherein the inflatable element 12 is insufflated to a medium level. In this way, the angle $\alpha_1$ formed between a longitudinal axis of the retractor shaft 18 and a predominant axis of the inflatable element 12 is greater than the angle α from FIG. 7.

Still, a further flattened compartment 24 is shown in FIG. 9, wherein the inflatable element 12 is insufflated to a high level. In this way, the angle $\alpha_2$ formed between a longitudinal axis of the retractor shaft 18 and a predominant axis of the inflatable element 12 is greater than the angle α from FIG. 7 and angle $\alpha_1$ from FIG. 8. Preferably, the angle α formed between a longitudinal axis of the retractor shaft 18 and a predominant axis of the inflatable element is between 0 and 90 degrees, and more preferably, between 20 and 70 degrees. Importantly, the angle must be chosen so that the retractor does not turn inside out during use. The optimum angle chosen will also depend upon the size, thickness and configuration of the inflatable element.

With reference, for example, to FIG. 7, the level of insufflating is under complete control of the surgeon by way of valve 22. By operating the valve 22, the surgeon may control the rate of insufflation, as well as the final rigidity and shape of the retractor 10. As such, the insufflation process may be operated in a gentle way to retract and separate intestines, even in the setting of adhesion. However, it should be understood that other types of mechanisms for insufflating the inflatable element may be used, depending upon application and design preference.

For example, a pressure indicator may be included, which indicates the pressure of the inflatable element 12. The pressure indicator may be correlated to the inflatable element 12, such that certain chambers of the inflatable element 12 collapse when the pressure exceeds a predetermined level. As such, the fully inflated element 12 allows for a built in load limiter which limits the load applied to the intestine. In addition, the correlation between the collapsing value and the internal pressure level may be preset, and the user should be instructed on what volume of air should be pumped into the trocar.

Figure 2:
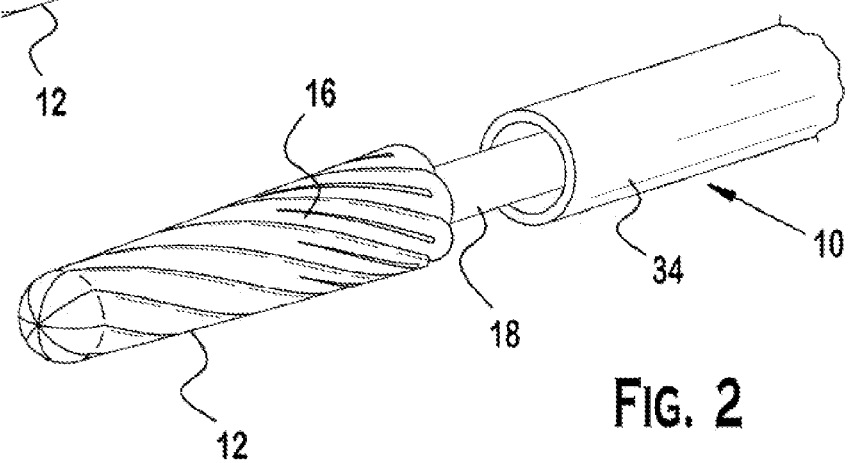
FIG. 2 illustrates a perspective view of an exemplary retractor, in part, according to the features of the present invention showing the commencement of deployment of the inflatable element.
Figure 6:
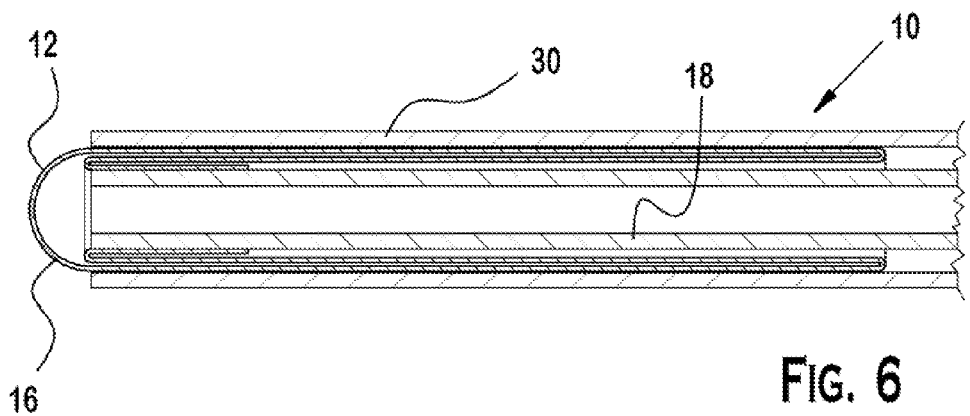
FIG. 6 illustrates a cross sectional view of the inflatable element positioned within an outer deployment shaft according to features of the present invention.

With reference to FIGS. 1, 2 and 6, deployment of the retractor 10 will be described in more detail. In particular, the inflatable element 12 may be housed in an outer deployment shaft 34. Preferably, the outer deployment shaft 34 is adapted to retain the inflatable element 12 therein when in the deflated condition, as shown, for example, in FIGS. 1, 2, and 6. In this way, the inflatable element 12 is positioned around the retractor shaft 18, and nestled within the inner channel of the outer deployment shaft 34.

With reference to FIGS. 11-14, the outer deployment shaft 34 may be constructed as a standard trocar-induced cannula. In particular, the outer deployment shaft 34 may include a cannula 36 at a distal or insertion end 38 for penetration into body of a patient, and a proximal end 40 having a cannula handle 42 maintained outside the body of the patient. The outer deployment shaft 34 may be made from a material that is easily sterilized, biocompatible, and durable, such as polyethylene, and the like.

While retractor 10 is illustrated in connection with an outer deployment shaft 34, it should be understood that the retractor 10 may be inserted inside any laparoscopic port without the use of the outer deployment shaft 34. In this way, the retractor is inserted directly into an existing port. As such, the retractor 10 is not limited to any particular housing or shaft, or method of insertion into a patient's body.

With reference to FIGS. 11-13, the retractor 10 may be deployed through a standard trocar, such as a 10/12 mm trocar, although any sized trocar is possible, depending upon application and design preference. For example, the retractor 10 may be designed to fit through 5 mm trocars to optimize efficiency.

With particular reference to FIG. 11, the retractor 10 may be inserted into a port 44 of the body 46 of a patient. In particular, the retractor 10 is moved out of the outer deployment shaft 34 towards the organ to be retracted. As described above, the outer deployment shaft 34 may be part of a trocar-induced cannula, but may also be a separate shaft, as shown, for example, in FIG. 4. During deployment of the retractor 10, the inflatable element 12 remains in a deflated condition. As described above, the surface roughness of the material of the inflatable element 12 preferably allows it to stay positioned about the retractor shaft 18 during deployment. This self-adhesive ability would also allow the inflatable element 12 to be deployed into an existing port without an outer deployment shaft, as described above.

With continued reference to FIG. 11, the retractor 10 is directed past the organ it is intended to retract. As shown in FIG. 11, the retractor 10 is positioned below the bowels 48. Once the retractor 10 is appropriately positioned, the surgeon operates valve 22 to inflate the inflatable element 12, as shown in FIG. 12. In particular, a pump 50 may be provided to direct insufflation fluid to the inflatable element 12. The inflatable element 12 may be filled with any type of fluid, including but not limited to, liquid such as saline and air such as $CO_2$. The pump 50 may be the same source providing $CO_2$ to insufflate the abdomen, or may be a separate source, depending on application or design preference. For example, a hand-held pump similar to one used to take blood pressure, may be provided. The pump preferably is designed to attach onto the insufflation port, which would allow a surgeon to manually pump the appropriate amount of fluid into the inflatable element.

Moreover, as described above, the surgeon controls the level of insufflation of the retractor 10 by controlling valve 22. That is, the retractor 10 may be filled to different levels, as shown for example, in FIGS. 7-9, with the final shape and rigidity of the inflatable element 12 depending on the amount of fluid that is insufflated into the system. As the inflatable element 12 is insufflated with fluid, the inflatable element 12 opens up and moves away from the retractor shaft 18, similar to the opening of an umbrella. Once the appropriate orientation, size, and rigidity are achieved, the inflatable element 12 is set to trap and hold the organs behind it.

With reference to FIG. 13, once the organs (and in this case, the bowels 48) are trapped within the inflatable element 12, the surgeon pulls back on the retractor shaft 18 to clear the field of view of the surgical area 52. As shown in FIG. 13, the retractor 10 may be secured into place by way of clamp 54. Preferably, the clamp 54 is circular and includes inner ridges (not shown) which mate with outer ridges 56 on the exterior surface of the retractor shaft 18, keeping the retractor 10 in place. The corresponding ridges allow the clamp to anchor the retractor 10 onto the outer deployment shaft 34 or cannula, without allowing it to slide. Preferably, the clamp 54 is hinged, and has a simple locking mechanism (such as a latch) to allow it to close circumferentially around the retractor shaft 18. When closed, the clamp 54 rests on top of the outer deployment shaft 34 or cannula and prevents the retractor 10 from sliding within the outer deployment shaft 34, thereby potentially obviating the need of additional assistance.

A laparoscope (not shown) can then be advanced either past the balloon, or through the windows 30 to keep it out of the visual field. In addition, one or more surgical tools 58 may be advanced through other ports via a cannula 59 or the like to perform the particular laparoscopic procedure. Once the operation is complete, the inflatable element 12 may be deflated by opening up valve 22, and removing the deflated inflatable element 12 from the body of the patient. Alternatively, the inflatable element 12 may be easily punctured, so that the insufflation fluid falls into the body of the patient, before the deflated inflatable element 12 is removed, allowing for quick removal.

The retractor 10 according to the features of the present invention is easily deployable and mobile. It has a variable shape and rigidity, which is controlled by the surgeon or assistant. As such, the retractor 10 may be particularly helpful to surgeons having high volumes, or who will be operating on deeper structures in the abdominal cavity or pelvis, where a still operative field is necessary for tine and intricate dissection. It also allows for consistent and atraumatic retraction of the adjacent organs for a safer and more efficient operation to be performed.

In addition, the retractor 10 of the present invention allows for the safe and consistent isolation and retraction of adjacent organs to allow clear visualization of the target organ of interest. It can be used in multiple quadrants of the abdomen, and will not cause injury to healthy intestines or solid organs. It is easily deployed through a laparoscopic port, and does not require advanced laparoscopic training to use.

EXAMPLE 1

Figure 14:
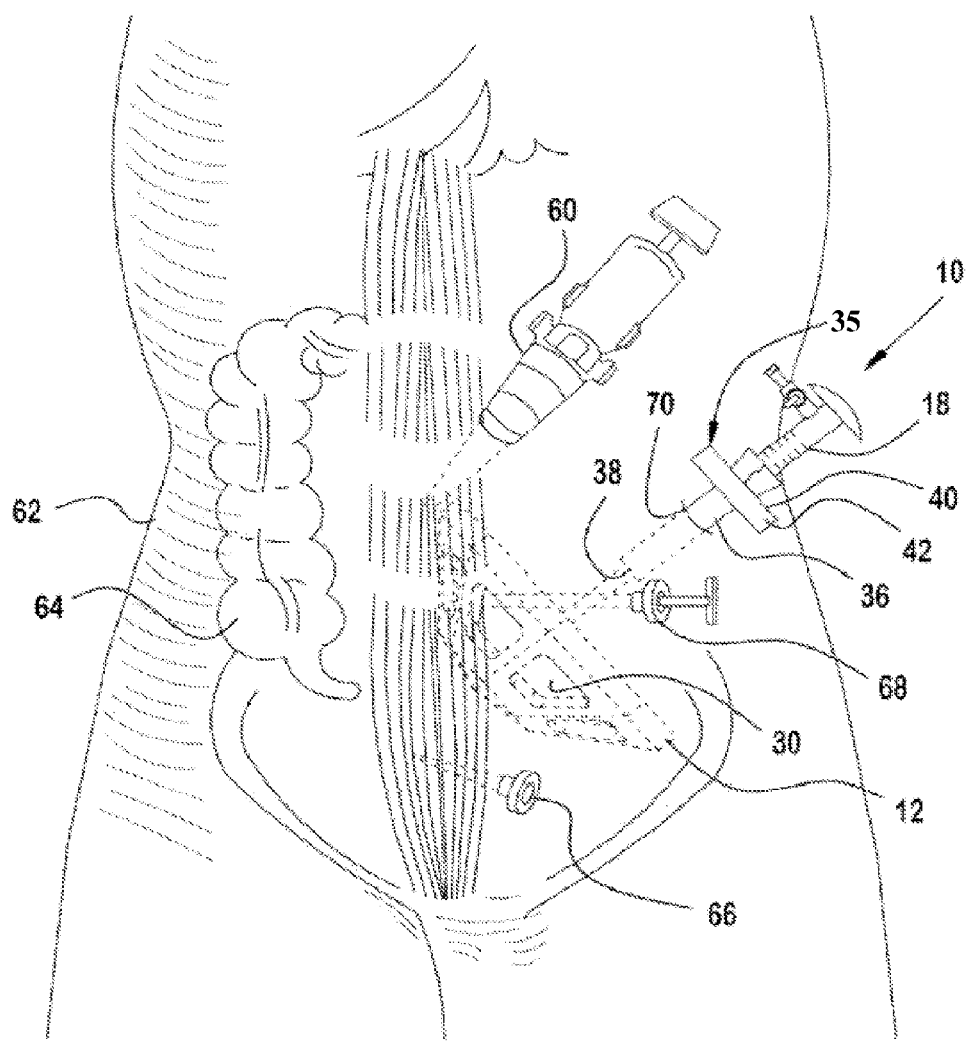
FIG. 14 illustrates a schematic view of a patient showing how the inflatable retractor of the present invention may be used during an appendectomy performed by laparoscopic surgery.

With reference to FIG. 14, use of the retractor 10 of the present invention is described in connection with abdominal surgery. In particular, the surgeon makes an infraumbilical incision with a Hasson trocar 60 and safely enters the abdominal cavity. The patient 62 has adhesions in the right lower quadrant of the abdomen due to an inflamed appendix 64. A first 5 mm trocar 66 is inserted in the supra-pubic position and a second 5 mm trocar 68 is placed into the left lower quadrant. The retractor 10 is deployed through an incision 70 in the left upper quadrant cannula 35, and graspers (not shown) are placed in the 5 mm trocars 66 and 68. The inflatable element 12 is brought into view. The intestines are retracted toward the left upper quadrant away from the appendix 64, and the inflatable element 12 is deployed by insufflation.

As the inflatable element 12 opens like a spiraling umbrella, the inflatable element 12 systematically traps the intestines behind it. The surgeon may help by gently positioning the intestines behind the inflatable element. The insufflation pressure of the inflatable element 12 is adjusted by the surgeon to provide adequate retraction and rigidity. The retractor 10 is then pulled back towards the left upper quadrant to create more space around the appendix 64. The laparoscope position may be adjusted so that the view is unimpeded by the retractor 10. This can be done by further retracting the inflatable element 12 away from the field, or by adjusting the scope so that it is looking through the windows 30 of the inflatable element 12. The appendix 64 is then clearly visualized, the operative field is free of cascading intestines and the operation is safely and efficiently performed. Once the appendix 64 is removed, the inflatable element 12 is desufflated and the retractor 10 is removed from the abdominal cavity.

While the inflatable retractor 10 has been described primarily in connection with retracting organs from the field of vision during laparoscopic surgery, it should be understood that it may have different uses, including but not limited to, as a dissection tool for the dissection of a target organ or adhesed planes. For example, the insufflating property of the retractor 10 will allow it to safely open adhesed planes in an atraumatic fashion. The retractor 10 may also be useful for hemostatis or tamponade bleeding. In particular, the inert material will allow it to be used as a compressive device to minimize bleeding from an injured vessel or gastrointestinal spillage from an enterotomy. The retractor 10 may also be used for thoracic surgery to isolate the lung or pulmonary vessel. However, it should be understood that the retractor 10 may have many different uses, depending upon application and design preference.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. An inflatable retractor, comprising:
an inflatable element including an inner surface and an outer surface;
a retractor shaft including a port for receiving insufflating pressure, said inflatable element being secured to a distal end of said retractor shaft;
wherein the inflatable element is configured so as to form a compartment when said inflatable element is insufflated with fluid,
wherein the compartment is concave towards the retractor shaft,
wherein the inflatable element is positioned around the retractor shaft in a deflated condition prior to first use.

2. The retractor of claim 1, wherein the compartment is v-shaped.

3. The retractor of claim 1, wherein the inflatable element includes a plurality of windows, and said windows are sufficiently large to enable a field of vision beyond the outer surface the retractor.

4. The retractor of claim 1, wherein the inner surface of the inflatable element includes raised bumps suitable to aid in attachment to tissue.

5. The retractor of claim 1, wherein said port is operatively connected to a valve for insufflating and desufflating of the inflatable element to a range of insufflating levels, wherein a configuration of said compartment changes according to an insufflating level of the range of said insufflating levels.

6. The retractor of claim 1, further including a clamp for releasably positioning the retractor into a fixed position after an organ is positioned within the compartment and retracted from a field of vision.

7. The refractor of claim 1, further including an outer deployment shaft, said outer deployment shaft disposed about said retractor shaft, and adapted to surround the inflatable element when in a deflated condition.

8. The retractor of claim 1, wherein the inner surface of the inflatable element is open towards the retractor shaft and the port.

9. The retractor of claim 1, wherein, when the inflatable element is insufflated with fluid, the inner surface of the inflatable element is open towards the retractor shaft, and the retractor shaft extends from the inner surface of the inflatable element towards the port.

10. The retractor of claim 1, the inflatable element having no sharp edges or hard substances.

11. The retractor of claim 1, wherein the retractor shaft is a rigid shaft suitable for causing tissue retraction by retraction of the shaft.

12. The retractor of claim 1, wherein the inflatable element is wrapped around the retractor shaft in a deflated condition.

13. The retractor of claim 1, wherein the compartment defines a concavity configured to receive tissue such that when the retractor shaft is pulled back, the inflatable element retracts tissue received within the concavity.

14. The retractor of claim 1, wherein a predominant axis of the inflatable element is configured to be at an angle selectable upon inflation from the range of 0-90 degrees relative to a longitudinal axis of the retractor shaft.

15. An inflatable retractor, comprising:
an inflatable element including at least a first chamber and a second chamber;
a retractor shaft including a port for receiving insufflating pressure, said inflatable element being secured to a distal end of said retractor shaft;
wherein the inflatable element is configured so as to form a compartment when said inflatable element is insufflated with fluid,
wherein the compartment is concave towards the retractor shaft,
wherein the retractor shaft is a rigid shaft suitable for causing tissue retraction by retraction of the shaft.

16. The inflatable retractor of claim 15, wherein the first chamber and second chamber are separately inflatable.

17. The inflatable retractor of claim 15, wherein the first chamber and second chamber are inflatable through a single port.

18. The retractor of claim 15, wherein the compartment is v-shaped.

19. The retractor of claim 15, wherein the inflatable element includes a plurality of windows, and said windows are sufficiently large to enable a field of vision beyond the outer surface the refractor.

20. The retractor of claim 15, wherein the inner surface of the inflatable element includes raised bumps suitable to aid in attachment to tissue.

21. The retractor of claim 15, wherein the inflatable element is positioned around the retractor shaft in a deflated condition prior to first use.

22. The retractor of claim 15, wherein said port is operatively connected to a valve for insufflating and desufflating of the inflatable element to a range of insufflating levels, wherein a configuration of said compartment changes according to an insufflating level of the range of insufflating levels.

23. The retractor of claim 15, further including a clamp for releasably positioning the retractor into a fixed position after an organ is positioned within the compartment and retracted from a field of vision.

24. The retractor of claim 15, further including an outer deployment shaft, said outer deployment shaft disposed about said retractor shaft, and adapted to surround the inflatable element when in a deflated condition.

25. An inflatable retractor, comprising:
an inflatable element including an inner surface and an outer surface;
a retractor shaft including a port for receiving insufflating pressure, said inflatable element being secured to a distal end of said retractor shaft;

an outer deployment shaft, said outer deployment shaft disposed about said retractor shaft, and adapted to surround the inflatable element when in a deflated condition, wherein the inflatable element is configured so as to form a compartment when said inflatable element is insufflated with fluid, wherein the compartment is concave towards the retractor shaft.

26. The retractor of claim 25, the inflatable element having no sharp edges or hard substances.

27. The retractor of claim 25, wherein a predominant axis of the inflatable element is configured to be at an angle selectable upon inflation from the range of 0-90 degrees relative to a longitudinal axis of the retractor shaft.

28. The retractor of claim 27, wherein said predominant axis of the inflatable element is configured to be at an angle of 90 degrees relative to a longitudinal axis of the retractor shaft.

29. The retractor of claim 25, wherein said inner surface of said inflatable element faces said retractor shaft, and wherein said inflatable element is configured to retract tissue contacting said inner surface.

30. The retractor of claim 25, wherein said inner surface of the inflatable element includes raised bumps suitable to aid in attachment to tissue.

31. The retractor of claim 25, wherein said inflatable element is made of an inert compound.

32. An inflatable retractor, comprising:

an inflatable element including at least a first chamber and a second chamber;

a retractor shaft including a port for receiving insufflating pressure, said inflatable element being secured to a distal end of said retractor shaft;

wherein the inflatable element is configured so as to form a compartment when said inflatable element is insufflated with fluid, wherein the compartment is concave towards the retractor shaft, wherein the first chamber and second chamber are separately inflatable.

* * * * *